(12) United States Patent
Klimant et al.

(10) Patent No.: US 6,303,386 B2
(45) Date of Patent: Oct. 16, 2001

(54) OPTICAL TEMPERATURE SENSORS AND OPTICAL-CHEMICAL SENSORS WITH OPTICAL TEMPERATURE COMPENSATION

(75) Inventors: Ingo Klimant, Regensburg; Gerhard Holst, Bremen, both of (DE)

(73) Assignee: Max-Planck-Gesellschaft zur Förderung der Wissenschaften e.V., München (DE)

( * ) Notice: Subject to any disclaimer, the term of this patent is extended or adjusted under 35 U.S.C. 154(b) by 0 days.

(21) Appl. No.: 09/091,907

(22) PCT Filed: Dec. 23, 1996

(86) PCT No.: PCT/EP96/05832

§ 371 Date: Jun. 24, 1998

§ 102(e) Date: Jun. 24, 1998

(87) PCT Pub. No.: WO97/24606

PCT Pub. Date: Jul. 10, 1997

(30) Foreign Application Priority Data

Dec. 27, 1995 (DE) .............................. 195 48 922

(51) Int. Cl.[7] .................................. G01N 21/64
(52) U.S. Cl. ................. 436/172; 436/68; 422/82.07
(58) Field of Search ................. 422/82.07, 82.08; 436/172, 68; 250/458.1, 459.1

(56) References Cited

U.S. PATENT DOCUMENTS

| 4,889,690 | * | 12/1989 | Opitz et al. ................. 422/73 |
| 4,895,156 |   | 1/1990  | Schulze . |
| 5,030,420 | * | 7/1991  | Bacon et al. ................. 422/82.07 |
| 5,108,932 |   | 4/1992  | Wolfbeis . |
| 5,115,811 | * | 5/1992  | Hartlaub et al. .................. 356/39 |
| 5,485,530 | * | 1/1996  | Lakowicz et al. ............... 250/459.1 |
| 5,728,422 | * | 3/1998  | Kane et al. ................. 422/82.07 |
| 5,783,152 | * | 7/1998  | Nave ................. 422/82.06 |

FOREIGN PATENT DOCUMENTS 357586    3/1990   (EP) .

OTHER PUBLICATIONS

Demas et al., *on the design of luminescence based* temperature sensors, SPIE, vol. 1796, pp. 71–75 (1992).
MacCraith et al., Fiber Optic Oxygen Sensor Based on Fluorescence Quenching of Evanescent–Wave Excited Ruthenium Complexes in Sol–Gel Derived Porous Coatings, Analyst, vol. 118, pp. 385–388 (Apr. 1993).

* cited by examiner

Primary Examiner—Jeffrey Snay
(74) Attorney, Agent, or Firm—Fulbright & Jaworski, LLP

(57) ABSTRACT

The invention relates to a device for the temperature-compensated determination of chemical parameters, comprising:
an optical temperature sensor which contains a temperature indicator that has a temperature-dependent afterglow time and/or luminous intensity and does not react with the surrounding medium; a chemical sensor which contains an indicator that is sensitive to a chemical parameter; means for stimulating the temperature indicator and the chemical indicator to luminesce; means for measuring the luminescence of the temperature indicator and of the chemical indicator; means for establishing an optical connection between indicator, excitation device and measuring equipment; means for detecting luminous radiation.

30 Claims, 1 Drawing Sheet

OPTICAL TEMPERATURE SENSORS AND OPTICAL-CHEMICAL SENSORS WITH OPTICAL TEMPERATURE COMPENSATION

BACKGROUND AND SUMMARY OF THE INVENTION

This invention relates to optical temperature sensors and optrodes with optical temperature compensation.

The determination of chemical parameters, eg, of the partial pressure of gases such as oxygen, carbon dioxide and ammonia, the pH, the concentration of dissolved ionic compounds, etc. by means of optical-chemical sensors (optrodes) is known. Like electrochemical sensors, these optrodes have a temperature-dependent response. Use of these sensors consequently requires simultaneous measurement of the specimen temperature and of the temperature in the chemically sensitive layer. For this purpose, use is made almost exclusively at present of electrical temperature sensors. This means, however, that a major advantage of optrodes, namely that they can be used in electromagnetic fields, is lost. In addition, combining an optical-chemical sensor with an electrical temperature sensor often makes it more expensive to manufacture the optrode. There is thus less advantage to be seen in using the optrode as a cheap, disposable sensor. Moreover, temperature compensation of measurements made with electrical temperature sensors is in many cases not feasible anyway.

So far, only few experiments have been described in which temperature compensation is achieved using optical means. The Israeli patent application IL-A-96 100 describes a process for determining a gas, a vapor, or a gas dissolved in a liquid specimen by means of a two-sensor system. The first sensor is a chemical sensor which contains a fluorescent reagent and is in contact with the measuring medium. The second sensor is a reference sensor which contains the same fluorescent reagent in a form isolated from the measuring medium.

U.S. Pat. No. 5,115,811 discloses a fiberoptic sensor for determining a parameter in a measuring medium. It contains a chemical sensor with a colorant composition whose optical properties correlate with the changes in the parameter to be determined. The sensor is coupled with a light source and with a device for measuring the light at three different wavelengths. The first wavelength is selected such that the optical properties of the colorant remain more or less constant despite changes in the parameter under analysis. The second and third wavelengths are selected such that the optical properties of the colorant vary in correlation with changes in the parameter under analysis and also as a function of the temperature. The light measured at the three wavelengths is evaluated to determine the temperature of the measuring medium, necessary in order to obtain temperature compensation for the parameter being determined.

Both the above-described procedures have the disadvantage that they only compensate for certain temperature effects, since they do not provide the means for absolute temperature measurements.

Austrian patent AT-B-393 326 relates to a method for the quantitative determination of at least one parameter in a liquid or gaseous specimen, with the fluorescent radiation emitted after excitation being measured in an indicator substance which is in direct or diffusion contact with the specimen, the change in a first parameter under analysis being obtained from the change in the ratio of two intensities determined at different wavelengths of the excitation or emission spectrum of the indicator substance and the change in a second parameter being obtained from the change in the afterglow time of the fluorescent radiation from the same indicator substance, selected from the group of aromatic hydrocarbons, aromatic heterocyclics and metallo-organic complexes. The disadvantage of this method consists in that, due to the use of just one indicator substance for determining two parameters, no independent measuring signals can be obtained for these two parameters. Consequently, no spectral separation is possible, nor is it possible to simultaneously measure the afterglow time for two parameters. Due to the fact that the indicator of the AT-B-393 326 is in contact with the measuring medium, interactions between components of the medium and the indicator can moreover lead to inaccurate results during a temperature determination. In practice, these disadvantages mean that the sensor described in the AT-B-393 326 is only of very limited use for the temperature-compensated measurement of chemical parameters.

The DE-C-32 13 183 relates to an arrangement for the optical determination of physical and chemical parameters of a system under test, with a photometric device having at least one radiation source, a monochromatic filter, an opto-receiver and a display device, and at least one indicator chamber which is separated from the system under test by a semi-permeable membrane and which contains an indicator that responds to the physical or chemical parameters under analysis by changing its spectral properties; the absorption capacity and the film thickness of the indicator are selected such that the side of the membrane in contact with the system under test is not reached by the test light. The arrangement can also include nano capsules as secondary indicator chambers, which contain indicators that respond to one or more additional physical or chemical properties with a change in their spectral characteristics. Liquid crystals which change color as the temperature changes are cited as examples of indicators in the nano capsules. The DE-C-32 13 183 does not disclose the use of indicators which are inert towards the medium and which have a temperature-dependent afterglow time and/or intensity of the luminescence.

There are some optical temperature sensors based on the temperature-dependent afterglow time of crystals or phosphors. These optical temperature sensors, however, have so far not been used in conjunction with chemical optrodes.

The use of luminescent metallo-organic compounds—eg, ruthenium complexes with heterocyclic nitrogen ligands—as oxygen indicators for optrodes is known (cf. eg, Wolfbeis et al., Mikrochim. Akta (Vienna) 1986, III, 359–366; Bacon and Demas, Anal. Chem. 1987, 59, 2780–2785; Carraway et al., Anal. Chem. 1991, 63, 337–342; McGraith et al., Analyst 1993, 118, 385–388). The basic idea of using luminescent ruthenium complexes as temperature indicators has already been suggested by Demas et al.(Proc. SPIE 1992, vol. 1796, 71–75). However, this publication does not contain any indication that it is possible to reference the temperature influence of optrodes in this way.

One of the objectives of this invention was to overcome—at least partially—the disadvantages of the methods known from prior art for measuring temperature and for the temperature-compensated determination of chemical parameters. In particular, the invention was intended to provide a method for the temperature-compensated determination of parameters which is easy to carry out and is not affected by strong electromagnetic fields.

The object of the invention is established by means of a device for the temperature-compensated determination of chemical parameters, comprising:

an optical temperature sensor which contains a temperature indicator that has a temperature-dependent afterglow time and/or intensity of the luminescence and does not react with the surrounding medium;

a chemical sensor which contains an indicator that is sensitive to a chemical parameter;

means for stimulating the temperature indicator and the chemical indicator to luminesce; means for measuring the luminescence of the temperature indicator and of the chemical indicator;

means for establishing an optical connection between indicator, excitation device and measuring equipment and means for detecting luminescent radiation.

DETAILED DESCRIPTION

As temperature indicator, use is made preferably of a luminescent metal complex with a temperature-dependent afterglow time and/or intensity of the luminescence. The luminescent metal complex is preferably a complex of a rare earth or transition metal with organic ligands. It is especially beneficial if the metal complex has the general formula (I):

$$M^{n+}(L_1L_2L_3)X^{n-} \qquad (I),$$

where M is a metal cation selected from the rare earths or transition metals, n is 2 or 3, $L_1$, $L_2$ and $L_3$ are the same or different and stand for ligands with at least two nitrogenous heterocyclic compounds which are connected via nitrogen atoms to the metal cation, and X stands for one or more negatively charged groups.

The metal cation is preferably ruthenium, osmium, rhenium, iridium, rhodium, platinum, palladium, molybdenum or chrome. Particular preference is given to ruthenium, iridium, rhenium, chrome and osmium. Most preference is given to ruthenium.

The ligands $L_1$, $L_2$ and $L_3$ are ligands with at least two nitrogenous heterocyclic compounds. Aromatic heterocyclics are preferred, such as bipyridyl, bipyrazyl, terpyridyl and phenanthroline. It is of particular advantage to select ligands $L_1$, $L_2$ and $L_3$ from bipyridyl and phenanthroline ring systems.

The metal complex also contains a negatively charged group. The negatively charged group can be a component of a ligand, or else a free counterion. Examples of suitable negatively charged groups are counterions such as perchlorate, organic sulfates, eg, lauryl sulfate, and organic carboxylates.

It is especially preferable if the temperature indicator is a ruthenium (II)-tris-1,10-phenanthroline complex, a ruthenium (II)-tris-4,7-diphenyl-1,10-phenanthroline complex or a ruthenium (II)-tris-2,2'-bipyridyl complex.

Instead of luminescent metal complexes use can also be made of other temperature-sensitive materials, eg, chrome (III)-YAG, alexandrite or manganese-doped magnesium fluorogermanate. These materials are phosphorescent solids which can be pulverized and dispersed in a matrix containing the chemical sensor. A disadvantage of these materials compared to the fluorescent metal complexes is that it is not possible to prepare thin transparent films for priming other optrodes. Besides this, the luminescent intensity is generally not as high due to weaker light absorption.

If it is to be sufficiently insensitive to chemical parameters such pH, oxygen or ionic compounds, the temperature indicator must be inert with respect to the surrounding medium. In a first embodiment of the invention, the temperature indicator is immobilized in a solid matrix, eg, an optically transparent polymer film. The solid matrix is prepared, for example, by applying a mixture of a glass or a polymer such as polyvinyl chloride, polyvinylidene chloride or polymethylmethacrylate, the dissolved indicator and a solvent to a substrate such as an optical fiber or a transparent film and then evaporating off the solvent. The matrix is preferably 1 μm to 20 μm thick, even more preferably 2 μm to 10 μm thick.

Alternatively, the temperature indicator can be enclosed in a vessel, eg, a glass microcapillary with an optical fiber attached near to its end. The indicator in the capillary can be in dissolved form.

The optical temperature sensor of the invention preferably exhibits a temperature-dependent change in quantum yield and/or in the afterglow time, while its cross-sensitivity towards oxygen and other chemical parameters is negligible. The sensor can be used within a temperature range from −50° C. to +50° C., in particular −20° C. to +50° C., and is easily made using familiar techniques.

It is preferable to select the temperature indicator such that the afterglow time has a temperature coefficient in the range from 5 to 100 ns, or, especially preferable, from 10 to 50 ns per ° C.

On account of its using at least two different indicators, one of which is inert with respect to the surrounding medium and serves to measure the temperature, the sensor of the invention allows an independent temperature measurement within itself. This is a decisive advantage over the optical sensors known from prior art and also over the thermocouples commonly in use at this time, which, especially in the case of measurements in the gas phase and at high light intensity, are apt to be inaccurate due to heating effects. Furthermore, the sensor of the invention for the first time provides a means of imaging, ie, making an areal measurement. This imaging can ensue within a lateral area of several square centimeters to square meters, eg, 10×5 cm. Up till now, only IR cameras could be used to do this, which are not accurate enough for this purpose. The technique of imaging is important especially in the field of medicine, eg, for measuring tumor tissue (tumor oxygenation) or transplanted tissue (vitality). Generally speaking, the sensors of the invention are suitable for all natural systems in which temperatures can vary.

Another advantage of the sensor of the invention is that it is compatible with semi-conductor components. Accordingly, use is made preferably of one or more electroluminescent diodes as the means to stimulate the metal complex to luminesce, and of one or more photodiodes as detector. It is preferable if the indicator, excitation and measuring equipment are optically interconnected by means of optical fibers, eg, fibers of quartz glass. If necessary, the optical temperature sensor can be provided with an optical screen so as to exclude the possibility of interference by light from the measuring medium. The signal is measured by means of a suitable detection system with which the temperature-dependent afterglow time or intensity is determined, eg, by means of a phase-modulation technique.

The temperature sensor of the invention is preferably combined with a chemical sensor which contains an optical-chemical indicator. This combination of an optrode with an optical temperature sensor serves to measure the temperature directly in the sensitive layer of the optrode and thus to effect a temperature compensation.

According to one embodiment of this invention, the temperature indicator and the chemical indicator are immobilized in different solid matrices, which means, eg, that the sensor is made up of two layers, a temperature-sensitive and a chemically sensitive layer. The temperature-sensitive layer is designed such that it does not exhibit any cross-sensitivity towards chemical measuring-medium parameters. The chemically sensitive layer, by contrast, is sensitive towards a measuring medium parameter, eg, oxygen. The temperature and chemical signals can be recorded as separate spectra by means of appropriate detector devices, or else they can be resolved chronologically. The temperature can be measured by way of determining the afterglow time and is thus not influenced by filter effects which may be caused by changes in the optical properties of the chemically sensitive layer. Since light absorption by the temperature-sensitive layer is associated with negligible temperature coefficients, the measuring signal of the chemical sensor is not affected.

Alternatively, the temperature and the chemical indicators can be immobilized in the same solid matrix, in which case one has a single-layer sensor. With this embodiment of the invention, it is preferable if the temperature indicator, which is inert towards the measuring medium, is dispersed within the matrix containing the chemical indicator.

Indicators for the chemically sensitive layer are known, eg, polycyclic aromatic hydrocarbons or transition metal complexes, and these have surprisingly also proved suitable for temperature determination according to the invention. By contrast to the temperature-sensitive layer, however, the chemically sensitive layer is designed in such a manner as to allow contact between the measuring medium and the indicator, a measuring signal being obtained which is based on the correlation between the luminescent intensity of the chemical indicator and the parameter to be determined.

Devices according to the invention, which allow the temperature-compensated, optical determination of parameters, are easy to make, eg, by applying one or more temperature- and/or chemically sensitive coatings to a substrate, eg, by means of spin coating, dip coating, screen printing etc.

It is preferable if the device according to the invention is designed such that the temperature indicator and the chemical sensor can be brought into direct contact with the measuring medium. In this way, a higher level of accuracy can be obtained, and therefore better temperature compensation.

It is of advantage to use substances which luminesce at different wavelengths as temperature indicator and as chemical sensor. It is thus preferable if the device of the invention is designed such that the means employed to stimulate luminescence operate at different wavelengths. An example of suitable luminescence excitation equipment is thus a combination of two or more electroluminescent diodes. As detection means, use is made preferably of two or more photodetectors which have different emission filters and thus allow the separate identification of luminescent radiation emitted by the temperature indicator and by the chemical indicator.

This invention also relates to a method for the temperature-compensated determination of chemical or physical parameters, in which an indicator that is sensitive towards a certain chemical parameter of the measuring medium is used together with a luminescent temperature indicator that is largely insensitive towards chemical parameters of the medium, and the signals produced by the two indicators are evaluated, characterized in that use is made of an optical temperature indicator, preferably a luminescent metal complex, which has a temperature-dependent afterglow time and/or intensity of the luminescence.

The method of the invention can also be performed as an areal determination, ie, in the form of imaging, preferably over an area of at least 1 cm$^2$, more preferably of 2–200 cm$^2$.

Particularly useful applications of this method are in the fields of medicine, biology or environmental engineering, eg, for analyzing gases such as $O_2$, $CO_2$, $NH_3$ etc. or dissolved ionic compounds, or for determining the pH.

As chemical sensor, use is made preferably of an optrode. Even in the presence of electromagnetic fields or interference, the method can be used for the simultaneous optical determination of temperature and of a chemical or physical parameter.

DETAILED DESCRIPTION OF PREFERRED EMBODIMENTS

Figure 1:
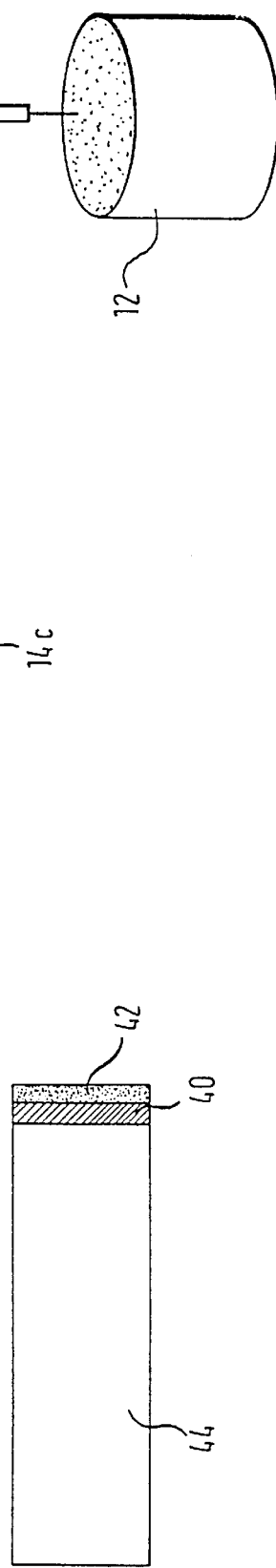
FIG. 1 shows an example of a device according to the invention for the temperature-compensated determination of chemical parameters, using a temperature indicator according to the invention and an optical-chemical indicator.

In FIG. 1 a combined temperature-sensitive and chemically sensitive micro-optrode (10) dips into a measuring medium (12), eg, a sediment core. The micro-optrode is connected via optical fibers (14) to a luminescence excitation and detection system (16). This system contains two LEDs (18a; 18b), eg, a blue and a yellow LED, with lenses (20a; 20b) and optical filters (22a; 22b), one of which generates light with a wavelength suitable to stimulate the temperature indicator to luminesce, and the other the chemical indicator. Electroluminescent diodes are preferred light sources because, compared to other light sources such as lasers or halogen or xenon lamps, they have the advantages of low price, small size, low power consumption and negligible heat generation. In addition, it is easy to electronically modulate the light emitted by an LED.

The light from the LEDs (18a; 18b) is bundled by the optical lenses (20a; 20b) and passed through the glass filters (22a; 22b) into an optical-fiber coupler (24), eg, a 1×4 optical-fiber coupler. The coupler serves to separate the energizing light being transmitted to the specimen from the luminescent signal returning from it.

Two optical fibers (14a; 14b) conduct the light generated by the LEDs to the optical-fiber coupler (24). The light then passes through optical fiber (14c) to the microsensor (10), where it stimulates the temperature and chemical indicators to luminesce. The optical fiber (14c) may contain an optical-fiber coupler (28).

The luminescent signal from the microsensor (10) travels back through optical fiber (14c) to the coupler (24) and from there it is conducted through two further optical fibers (14d; 14e) to two photodetectors (26a; 26b) in which the measuring signal is received. The photodetectors (26a; 26b) have different emission filters (30a; 30b), so that one detector receives the luminescent radiation from the temperature indicator and the other that from the chemical indicator.

The signals are preferably evaluated in an electronic control and signal-amplification unit. From there the signal is passed to a recording device.

Figure 2:
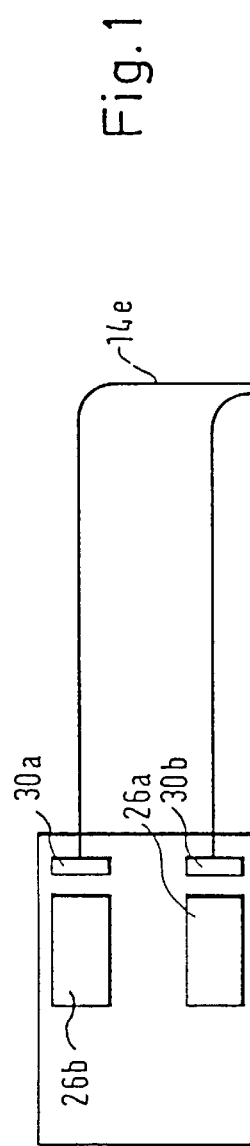
FIG. 2 shows an example of a sensor which contains both a temperature indicator and a chemical indicator.

FIG. 2 shows an example of a microsensor which contains both a temperature indicator and a chemical indicator. The sensor is a two-layer sensor which contains a temperature-sensitive film (40) with the temperature indicator and a chemically sensitive film (42) with the chemical indicator. A waveguide (44) provides the optical connection with a light source and a detector.

The following examples serve to explain the invention in more detail.

EXAMPLE 1

Preparation of Temperature Indicators 1.1 Ruthenium—(phenanthroline)$_3$—(lauryl sulfate)$_2$ 200 mg of ruthenium (II)-tris-1,10-phenanthroline dichloride (Ru(phen)$_3$Cl$_2$) from Aldrich (Steinheim, Germany) were dissolved in 100 ml of distilled water. Following addition of 50 ml of a solution of 10 mmol/l sodium lauryl sulfate in water, a finely dispersed precipitate was obtained. Then 20 ml of a 1 mol/l sodium chloride solution were added and after 3 hours the precipitate was filtered off. The resulting complex was washed with distilled water and diethyl ether before being dried for 24 h under vacuum at 30° C. The indicator was obtained as an orange-colored powder, yield 80 to 85%.

1.2 Ruthenium—(4,7-diphenyl-1,10-phenanthroline)$_3$—(dilauryl sulfate)$_2$ 225.9 mg RuCl$_3$ 3 H$_2$O (Aldrich) were dissolved in a mixture of 5 ml of ethylene glycol and 0.5 ml water at 120° C. Then 862.6 mg of 4.7 diphenyl-1,10-phenanthroline (dpp) (Aldrich) were added. The mixture was heated under reflux for 45 min. at 165° C. After it had cooled, the solution was taken up in 50 ml of acetone, filtered and diluted with acetone. The filtrate contains the crude product Ru (dpp)$_3$Cl$_2$. 100 ml of a 10 mmol/l aqueous solution of sodium lauryl sulfate were added to 100 ml of the filtrate. Finally, 100 ml of a 1 mol/l sodium chloride solution were added. The orange-colored precipitate was filtered and washed 4 times with distilled water. Additional purification was effected by recrystallization from an acetone-water mixture (18/20, V/V). The precipitate was then washed with diethyl ether and dried at 40° C. under vacuum. The product was obtained as an orange powder, yield 75 to 85%.

EXAMPLE 2

The temperature-sensitive layer was prepared by applying a mixture of a polymeric matrix, the dissolved indicator and a solvent to a substrate, eg, an optical fiber or a transparent film, and then evaporating off the solvent.

In this way, a ruthenium (II)-tris-1,10-phenanthroline dilauryl sulfate temperature indicator was prepared in a PVC matrix with a film thickness of 5 μm. The indicator is contained in dissolved form in the polymer, or the sensor layer is completely transparent.

The sensor exhibits no cross-sensitivity towards chemical parameters such as pH, oxygen, ionic compounds etc. The temperature coefficient of the afterglow time is approximately 25 ns per ° C. or 2.5% per ° C. The temperature indicator is strongly luminescent and is compatible with semiconductor components.

EXAMPLE 3

Combination of a temperature indicator and a chemical-optical indicator.

An optical oxygen sensor with intrinsic temperature compensation was prepared in the form of a two-layer sensor. The first layer is a temperature-sensitive layer of the kind described in Example 2. The second layer is an oxygen-sensitive layer with a phosphorescent platinum-porphyrin complex, dissolved in polystyrene.

The two measuring signals can be received as separate spectra and evaluated. Measurement is effected by means of the afterglow time and also the intensity of the luminescence.

What is claimed is:

1. A device for the temperature-compensated determination of chemical parameters, comprising:
    an optical temperature sensor which contains a temperature indicator that has a temperature-dependent afterglow time and/or intensity of the luminescence and does not react with the surrounding medium, wherein said temperature indicator is present in a matrix which does not permit said temperature indicator to contact said surrounding medium;
    a chemical sensor which contains a chemical indicator that is sensitive to a chemical parameter;
    means for stimulating the temperature indicator and the chemical indicator to luminesce;
    means for measuring the luminescence of the temperature indicator and the chemical indicator; and
    means for establishing an optical connection between each of said respective indicators, said stimulation means and said measuring means;
    wherein said temperature indicator is different from said chemical indicator and both the temperature indicator and the chemical indicator are arranged within a optical sensor, wherein said chemical indicator is present in a matrix which permits said chemical indicator to contact said surrounding medium.

2. The device of claim 1,
wherein
    the optical temperature sensor comprises a luminescent metal complex.

3. The device of claim 1, wherein the optical temperature sensor comprises a metal complex of formula I:

$$M^{n+}(L_1L_2L_3)X^{n-} \qquad I,$$

wherein M is a metal cation selected from the group consisting of rare earth metals and transition metals, n is 2 or 3, $L_1$, $L_2$ and $L_3$ are the same or different ligands with at least two nitrogenous heterocyclic compounds which are connected to the metal cation via nitrogen atoms, and X is at least one negatively charged group.

4. The device of claim 3 wherein said metal cation is ruthenium.

5. The device of claim 3, wherein said ligands of the metal complex are selected from nitrogenous aromatic heterocyclics.

6. The device of claim 5, wherein said ligands are selected from the group consisting of bipyridyl, bipyrazyl, terpyridyl and phenanthroline ring systems.

7. The device of claim 6, wherein said ligands are selected from the group consisting of bipyridyl and phenanthroline ring systems.

8. The device of claim 3, wherein said negatively charged groups are selected from the group consisting of perchlorate, organic sulfates and organic carboxylates.

9. The device of claim 1, wherein the temperature indicator comprises a complex selected from a ruthenium (II)-tris-1,10-phenanthroline complex, a ruthenium (II)-tris-4,7-diphenyl-1,10-phenanthroline complex and a ruthenium (II)-tris-2,2'-bipyridyl complex.

10. The device of claim 1, wherein said optical temperature sensor exhibits a temperature-dependent afterglow time.

11. The device of claim 10, wherein said afterglow time of the temperature indicator is temperature-dependent within the range from −50° C. to +50° C.

12. The device of claim 10, wherein said afterglow time of the temperature indicator has a temperature coefficient in the range from 5 to 100 ns per ° C.

13. The device of claim 1, wherein said optical temperature sensor has a temperature-dependent luminescent quantum yield.

14. The device of claim 1, wherein said means for stimulating the temperature indicator to luminesce comprises at least one electroluminescent diode.

15. The device of claim 1, wherein said means for measuring the afterglow time comprises at least one photodiode.

16. The device of claim 1, wherein the connection means comprises optical fibers.

17. The device of claim 1, wherein said temperature indicator is immobilized in a solid matrix.

18. The device of claim 17, wherein said matrix is an optically transparent polymer film.

19. The device of claim 1, wherein the temperature indicator is enclosed in a vessel.

20. The device of claim 19, wherein the vessel is a microcapillary vessel.

21. The device of claim 1, wherein said chemical sensor comprises an optrode with an optical-chemical indicator.

22. The device of claim 21, wherein said temperature indicator and said chemical indicator are immobilized in different solid matrices.

23. The device of claim 22, wherein said temperature indicator and said chemical indicator are immobilized in the same solid matrix.

24. The device of claim 23, wherein said temperature indicator is in a form which is inert towards the measuring medium and is dispersed within said matrix containing said chemical indicator.

25. A method for the temperature-compensated determination of chemical parameters, comprising contacting the device of claim 1 with the medium to be measured, and measuring the luminescence of the temperature indicator and chemical indicator.

26. The method of claim 25, wherein
a gas, the pH or dissolved ionic compounds are determined.

27. The method of claim 26, wherein
$O_2$ is determined.

28. The method of claim 25, wherein said chemical indicator comprises an optrode.

29. The of claim 25, wherein the method is conducted in the presence of electromagnetic fields.

30. The method of claim 25, wherein an areal analysis is conducted.

* * * * *